United States Patent
Lee et al.

(10) Patent No.: US 10,829,430 B2
(45) Date of Patent: Nov. 10, 2020

(54) ESTER COMPOSITION PREPARATION SYSTEM AND ESTER COMPOSITION PREPARATION METHOD USING SAME

(71) Applicant: LG CHEM, LTD., Seoul (KR)

(72) Inventors: Ha Na Lee, Daejeon (KR); Sung Kyu Lee, Daejeon (KR); Joon Ho Shin, Daejeon (KR); Hyoung Jun, Daejeon (KR); Hyun Kyu Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 16/343,988

(22) PCT Filed: Sep. 5, 2018

(86) PCT No.: PCT/KR2018/010385
§ 371 (c)(1),
(2) Date: Apr. 22, 2019

(87) PCT Pub. No.: WO2019/050281
PCT Pub. Date: Mar. 14, 2019

(65) Prior Publication Data
US 2019/0263745 A1 Aug. 29, 2019

(30) Foreign Application Priority Data

Sep. 7, 2017 (KR) .................. 10-2017-0114624

(51) Int. Cl.
*B01D 3/00* (2006.01)
*C07C 67/02* (2006.01)
(Continued)

(52) U.S. Cl.
CPC ............. *C07C 67/08* (2013.01); *B01D 3/009* (2013.01); *C07C 29/80* (2013.01); *C07C 67/02* (2013.01);
(Continued)

(58) Field of Classification Search
CPC ......... C07C 67/08; C07C 29/80; C07C 67/03; C07C 67/02; C07C 67/54; C07C 69/82; B01D 3/009
(Continued)

(56) References Cited

U.S. PATENT DOCUMENTS

2005/0274065 A1* 12/2005 Portnoff .................. C07C 67/08
44/605
2006/0178524 A1 8/2006 Zuber et al.
(Continued)

FOREIGN PATENT DOCUMENTS

EP 2851393 A1 3/2015
JP 61-016948 A 1/1986
(Continued)

OTHER PUBLICATIONS

N. R. Janjua et al., Systemic Uptake of Diethyl Phthalate, Dibutyl Phthalate, and Butyl Paraben Following Whole-body Topical Application and Reproductive and Thyroid Hormone Levels in Humans, Environmental Science and Technology, 2007, 41, pp. 5564-5570.
(Continued)

*Primary Examiner* — Huy Tram Nguyen
(74) *Attorney, Agent, or Firm* — Dentons US LLP

(57) ABSTRACT

Provided are an ester composition preparation system, including an integrated reactor, a gas-liquid separation column, a purification unit, an alcohol storage tank, and a mixed alcohol separation column, which is an efficient, economical, and simplified ester composition preparation system, and an ester composition preparation method using the same. The ester composition preparation system is a simplified system which can reduce facility space, drastically remove reaction equipment, and reduce transfer time through the introduction of the integrated reactor in which the reaction preparing an ester compound and the reaction (Continued)

preparing an ester composition are carried out in one space, the mixed alcohol separation column and the gas-liquid separation column.

10 Claims, 2 Drawing Sheets

(51) Int. Cl.
| | | |
|---|---|---|
| *C07C 67/54* | (2006.01) | |
| *C07C 69/82* | (2006.01) | |
| *C07C 67/08* | (2006.01) | |
| *C07C 29/80* | (2006.01) | |
| *C07C 67/03* | (2006.01) | |

(52) U.S. Cl.
CPC .............. *C07C 67/03* (2013.01); *C07C 67/54* (2013.01); *C07C 69/82* (2013.01)

(58) Field of Classification Search
USPC ........................................................ 422/187
See application file for complete search history.

(56) References Cited

U.S. PATENT DOCUMENTS

| | | |
|---|---|---|
| 2008/0139779 A1 | 8/2008 | Debruin |
| 2011/0251420 A1 | 10/2011 | Disteldorf et al. |
| 2015/0141691 A1 | 5/2015 | Disteldorf et al. |
| 2016/0194267 A1 | 7/2016 | Backes et al. |

FOREIGN PATENT DOCUMENTS

| | | | |
|---|---|---|---|
| JP | 07-309809 A | 11/1995 | |
| KR | 1020060090764 A | 5/2006 | |
| KR | 1020110101205 A | 9/2011 | |
| KR | 1020130051453 A | 5/2013 | |
| KR | 101354141 B | 1/2014 | |
| KR | 1020160055178 A | 5/2016 | |
| WO | WO-2010010111 A1 * | 1/2010 | ............ C11C 3/003 |

OTHER PUBLICATIONS

Mustafizur Rahman et al., The plasticizer market: an assessment of traditional plasticizers and research trends to meet new challenges, Progress in Polymer Science, 2004, 29, pp. 1223-1248.

* cited by examiner

PRIOR ART

US 10,829,430 B2

ESTER COMPOSITION PREPARATION SYSTEM AND ESTER COMPOSITION PREPARATION METHOD USING SAME

CROSS-REFERENCE TO RELATED APPLICATIONS

This application is a U.S. National Phase Application of International Application No. PCT/KR2018/010385, filed on, Sep. 5, 2018, which claims the benefit of priority based on Korean Patent Application No. 10-2017-0114624, filed on 7 Sep. 2017, the entire disclosure of which is incorporated as part of the specification.

TECHNICAL FIELD

The present invention an ester composition preparation system using an integrated reactor and an ester composition preparation method using the same.

BACKGROUND ART

A phthalate-based plasticizer accounts for 92% of the global plasticizer market (see Mustafizur Rahman and Christopher S. Brazel, Progress in Polymer Science 2004, 29, 1223-1248, "The plasticizer market: an assessment of traditional plasticizers and research trends to meet new challenges"). It is an additive used for imparting flexibility, durability and cold resistance mainly to polyvinyl chloride (hereinafter referred to as PVC) and lowering the viscosity during melting to improve processability. It is added in various amounts to PVC and widely used in various applications from rigid products such as rigid pipes to soft products which can be used for such as food packaging materials, blood bags, flooring materials, etc. due to its soft and good flexibility. Therefore, it is more closely related to real life than any other material, and the direct contact with the human body may not avoidable.

However, despite the compatibility of the phthalate-based plasticizer with PVC and its excellent capability to impart flexibility, it has been argued recently about harmfulness of the PVC product containing the phthalate-based plasticizer that the phthalate-based plasticizer can leak out of the PVC product when used in real life, and act as a presumed endocrine disrupting (environmental hormone) substance and a carcinogen of the level of heavy metals (see N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2008, 42, 7522-7527). Especially, since the report about the leakage of di-(2-ethyl hexyl) phthalate (DEHP), which was the most used phthalate-based plasticizer in the US in the 1960s, out of the PVC product, the interest in environmental hormones have been added in the 1990s and global environmental regulations as well as various studies on hazards of the phthalate-based plasticizer to human have been started.

Therefore, in order to cope with environmental hormone problems and environmental regulations due to the leakage of the phthalate-based plasticizer, many researchers have been conducting research to develop a new, alternative, non-phthalate-based plasticizer which is free of phthalic anhydride used in the production of phthalate-based plasticizers or a leakage inhibition technology which may inhibit the leakage of the phthalate-based plasticizer to greatly reduce the hazards to human and be in accordance with environmental standards.

Meanwhile, as a non-phthalate-based plasticizer, a terephthalate-based plasticizer has been getting the spotlight, because it is equivalent to the phthalate-based plasticizer in terms of physical properties, but is free of environmental issues. A variety of terephthalate-based plasticizers have been developed and research on the development of a terephthalate-based plasticizer having excellent physical properties, as well as researches on facilities for preparing such the terephthalate-based plasticizer have been actively conducted. In terms of process design, more efficient, economical and simple process design has been required.

PRIOR ART DOCUMENTS

Patent Document
(Patent Document 1) Korean Patent No. 10-1354141

Non-Patent Documents (Non-patent Document 1) Mustafizur Rahman and Christopher S. Brazel "The plasticizer market: an assessment of traditional plasticizers and research trends to meet new challenges" Progress in Polymer Science 2004, 29, 1223-1248

(Non-patent Document 2) N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2008, 42, 7522-7527

DISCLOSURE OF THE INVENTION

Technical Problem

An aspect of the present invention provides an efficient, economical, and simplified ester composition preparation system. An aspect of the present invention provides a simplified ester composition preparation system, which can reduce facility space, drastically remove reaction equipment, and reduce transfer time through the introduction of an integrated reactor in which the reaction preparing an ester compound and the reaction preparing an ester composition are carried out in one space, a mixed alcohol separation column and a gas-liquid separation column, and an ester composition preparation method using the same.

Technical Solution

According to an embodiment of the present invention, there is provided a preparation system, including: an integrated reactor having an inner reaction space in which the direct esterification, which is the reaction of a first alcohol and a carboxylic acid-based compound including two or more carboxyl groups, and the trans-esterification, which is the reaction of the product of the direct esterification and a second alcohol, are carried out, an upper outlet line connected to a gas phase compartment, and a lower outlet line connected to a liquid phase compartment, provided therewith; a gas-liquid separation column having a gas-liquid separation space, into which a gasified reaction product and a gas phase low boiling point mixture from the integrated reactor flow through the upper outlet line of the integrated reactor and in which the gas-liquid separation is carried out, a lower recovery line, through which a liquefied reaction product is recovered to the integrated reactor, and an upper outflow line, through which the gas phase low boiling point mixture flows out, provided therewith; a purification unit having a purification bath, in which an ester composition flowed out through the lower outlet line of the integrated reactor and the second alcohol are separated, a purified product line through which a purified ester composition is discharged, and an alcohol recovery line through which the second alcohol is recovered, provided therewith; an alcohol storage tank having an inner space, in which the first alcohol and the second alcohol are stored, provided therewith, and connected to the upper outflow line of the gas-liquid separation column and to the alcohol recovery line of the purification unit, so as to store a mixed alcohol of the first alcohol and the second alcohol; and a mixed alcohol separation column having an alcohol separation space, into which the mixed alcohol flows from the alcohol tank and in which the mixed alcohol is separated depending on the number of alkyl carbon atoms of the alcohol, and one or more recirculation lines, through which separated alcohol is recirculated, provided therewith, wherein the reaction product in the gas-liquid separation column is a product of the direct esterification or a product of the trans-esterification, and the low boiling point mixture includes one or more of the first alcohol and the second alcohol.

Advantageous Effects

The present invention can reduce facility space, drastically remove reaction equipment, and reduce transfer time, and thus, can provide an efficient, economical, and simplified ester composition preparation system and an ester composition preparation method using the same.

MODE FOR CARRYING OUT THE INVENTION

Figure 1:
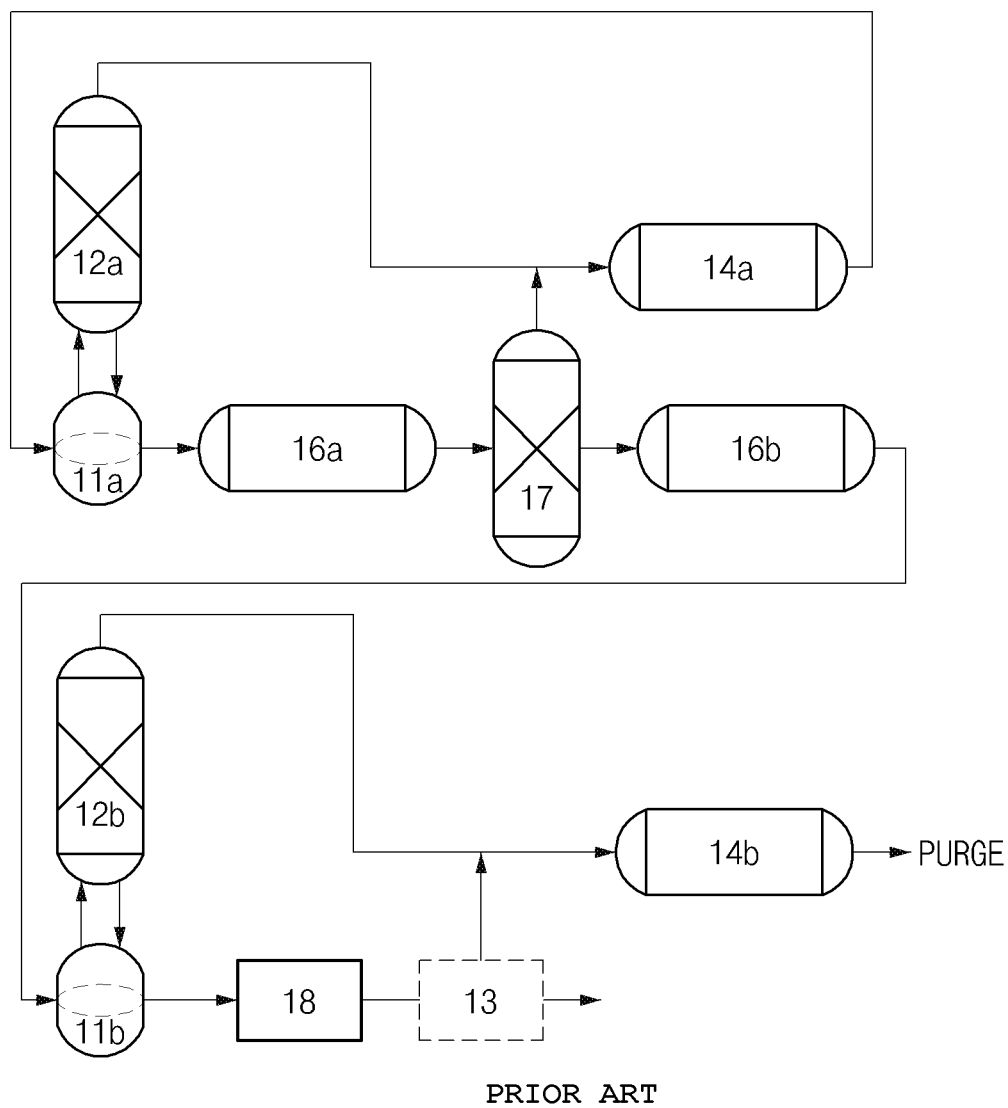
FIG. 1 is a process flow chart illustrating an example of a conventional process for preparing an ester composition.

Hereinafter, the present invention will be described in more detail to help an understanding of the present invention.

The terms or words used in the description of the present invention and claims shall not be interpreted as being limited to ordinary or dictionary meanings and the terms or words should be interpreted as meanings and concepts consistent with the technical idea of the present invention, based on the principle that an inventor may properly define the concept of a term to explain his own invention in the best way.

Ester Composition Preparation System

According to an aspect of the present invention, there is provided a preparation system, including: an integrated reactor; a gas-liquid separation column; a purification unit; an alcohol storage tank; and a mixed alcohol separation system.

Specifically, the integrated reactor has an inner reaction space in which the direct esterification, which is the reaction of a first alcohol and a carboxylic acid-based compound comprising two or more carboxyl groups, and the trans-esterification, which is the reaction of the product of the direct esterification and a second alcohol, are carried out, an upper outlet line connected to a gas phase compartment, and a lower outlet line connected to a liquid phase compartment, provided therewith.

In addition, the gas-liquid separation column has a gas-liquid separation space, into which a gasified product of the direct esterification and a gas phase low boiling point mixture from the integrated reactor flow through the upper outlet line of the integrated reactor and in which the gas-liquid separation is carried out, a lower recovery line, through which a liquefied product of the direct esterification is recovered to the integrated reactor, and an upper outflow line, through which the gas phase low boiling point mixture including the first alcohol flows out, provided therewith.

During the direct esterification, water and the first alcohol are included in the gas phase low boiling point mixture flowing out through the upper outlet line, and the water and the first alcohol are separated from each other through reflux and decanting, and then the first alcohol may be recovered to the reactor. After the end of the direct esterification and before the trans-esterification, the first alcohol is included in the gas phase low boiling point mixture flowing out through the upper outlet line and thus, the first alcohol may be removed. During the trans-esterification, small amounts of the first alcohol and the second alcohol are included in the gas phase low boiling point mixture flowing out through the upper outlet line, and thus, the first alcohol and the second alcohol may be recovered to the reactor through reflux.

In addition, the preparation system may further have a middle outlet line, which is a line connected to the liquid phase compartment in the integrated reactor. The middle outlet line is connected to the side part of the gas-liquid separation column and specifically, it may be connected to the side part at one half or higher in the height direction of the gas-liquid separation column.

As gas phase materials flow to the gas-liquid separation column through the upper outlet line, so through the middle outlet line, liquid phase materials may flow to the gas-liquid separation column. Specifically, the liquid phase reaction product and the ungasified low boiling point mixture may flow to the gas-liquid separation column through the middle outlet line.

Having the middle outlet line provided may have advantages such as maximization of the gas-liquid separation efficiency by the use of the gas-liquid separation column, process time reduction due to the improvement of separation efficiency, optimization of the removal level of the material to be removed, etc.

The purification unit has a purification bath, in which an ester composition flowed out through the lower outlet line of the integrated reactor and the first alcohol and the second alcohol are separated, a purified product line through which a purified ester composition is discharged, and an alcohol recovery line through which the first alcohol and the second alcohol are recovered, provided therewith, and the alcohol storage tank has an inner space, in which the first alcohol and the second alcohol are stored, provided with, and is connected to the upper outflow line of the gas-liquid separation column and to the alcohol recovery line of the purification unit, so as to store a mixed alcohol of the first alcohol and the second alcohol.

The purification unit may perform purification by using equipment including one or more purification baths and condensers, etc., and an appropriate number of equipment may be applied to the purification unit depending on a desired degree of purity, and in some cases, a distillation column may be disposed thereto. Each equipment may be, but not particularly limited to, one generally used for purification in the art.

The mixed alcohol separation column has an alcohol separation space, into which the mixed alcohol flows from the alcohol tank and in which the mixed alcohol is separated depending on the number of alkyl carbon atoms of the alcohol, one or more recirculation lines, through which separated alcohol is recirculated, and one discharge line, provided therewith.

In addition, the one or more recirculation lines of the mixed alcohol separation column may preferably be two recirculation lines. They may be a first alcohol recirculation line through which the first alcohol is recirculated to the integrated reactor and a second alcohol recirculation line through which the second alcohol is recirculated to the integrated reactor. The one discharge line may be a line through which water is discharged.

The ester composition preparation system according to the present invention does not discard mixtures of two kinds of alcohol and water, but can separate and reuse them by introducing the mixed alcohol separation column, thereby improving economic efficiency.

In addition, the preparation system may further include a product storage tank, wherein the product storage tank may be connected to the purified product line of the purification unit.

According to one embodiment of the present invention, the preparation system may be a batch reaction system, wherein the process such as alcohol recovery and the like may be carried out after one cycle.

In addition, preferably, the carboxylic acid-based compound including two or more carboxyl groups as a raw material for the direct esterification may be terephthalic acid. The first alcohol and the second alcohol may be primary alcohols, and it may be preferable that the number of —OH group is one. For example, in the case of two or more —OH groups, it is apprehended that polymerization toward polyester may proceed. Thus, it may not be compatible for the process conditions applied in the preparation system according to the present invention, and due to the polymerization, fouling in the reactor may occur. In addition, it is deviated from the object of the present invention of obtaining an ester composition. Accordingly, it is preferable that the first alcohol and the second alcohol are primary alcohols and ones having one —OH group.

In addition, the first alcohol and the second alcohol each may have different number of alkyl carbon atoms. The number of alkyl carbon atoms of the first alcohol may be larger than that of the second alcohol. Alcohol having an alkyl group having 1 to 12 carbon atoms may be applied. Preferably, the number of the alkyl carbon atoms of the first alcohol may be 6 to 12 and that of the second alcohol may be 1 to 5. More preferably, the number of the alkyl carbon atoms of the first alcohol may be 7 to 10 and that of the second alcohol may be 2 to 4.

The targeted product in the preparation system according to an embodiment of the present invention is an ester composition, which may include three kinds of ester compounds. Preferably, it may be a terephthalate composition including three kinds of terephthalates.

Hereinafter, an example of the present invention will be described in detail with reference to the accompanying drawings.

FIG. 1 illustrates an example of a process flow chart of a conventional system for preparing an ester composition. The conventional system for preparing an ester composition can be largely divided into two phases, which may be the first phase of the direct esterification process for preparing an ester compound and the second phase of the trans-esterification process for preparing an ester composition using the ester compound. Generally, the two processes were carried out separately.

Specifically, in the case of the first phase of the direct esterification process, in the first reactor 11a, the direct esterification of the first alcohol with the carboxylic acid-based compound including two or more carboxyl groups is carried out, and after the end of the direct esterification, the first alcohol and water are removed by the use of the first gas-liquid separation column 12a. Herein, the removed first alcohol flows into the first alcohol storage tank 14a. In the first alcohol storage tank 14a, the first alcohol is stored and when the entire one cycle process is completed, the first alcohol is supplied again to the first reactor 11a.

A stream, including the ester compound produced by the direct esterification together with by-products such as the unreacted first alcohol and the like, flows out from the first reactor 11a into the first buffer tank 16a. The first buffer tank 16a can control the flow of products and by-products in accordance with the separation capacity of the unreacted first alcohol removal column 17 and sends the unreacted first alcohol suitable for the separation capacity to the unreacted first alcohol removal column 17, so as to remove the unreacted first alcohol.

In the regard that the reaction in the first reactor 11a and the gas-liquid separation column 12a at the preceding stage is carried out in batch mode and the reaction in the first alcohol removal column 17 at the subsequent stage is carried out in continuous mode, the first buffer tank 16a can serve to link the batch process and the continuous process.

Subsequently, the product stream having the unreacted first alcohol removed therefrom, that is, including the ester compound, flows again into the second buffer tank 16b. The second buffer tank 16b serves to store the ester compound, which is the product of the direct esterification, and supplies the ester compound to the second reactor 11b where the trans-esterification takes place. Herein, the removed, unreacted first alcohol is recovered to the alcohol storage tank 14a.

Herein, in the regard that the alcohol removal process is carried out continuously at the preceding stage of the second buffer tank 16b and the trans-esterification reaction, which is the batch reaction, proceeds in the second reactor 11b at the subsequent stage of the second buffer tank 16b, the second buffer tank 16b may also be a device for linking the continuous process and the batch process.

The trans-esterification process of the second phase proceeds similarly to the direct esterification process, and the trans-esterification reaction of the ester compound and the second alcohol in the second reactor 11b produces an ester composition. Similarly as in the direct esterification process, when the reaction is completed, the unreacted second alcohol and the first alcohol, which is the product (byproduct) of the trans-esterification reaction, are removed through the second gas-liquid separation column 12b and recovered to the mixed alcohol tank 14b.

In addition, when the reaction is completed and the product stream is discharged from the reactor, this stream may flow into the neutralizer 18 and the purification part 13, so that the product may be purified through facilities for purification. In FIG. 1, the neutralizer 18 and the purification part 13 are shown as separate devices, but these may be integrated into one facility.

Although such conventional ester composition preparation process has many redundant facilities and many similar processes, it could not apply the integrated facility due to reduction in the efficiency of gas-liquid separation when alcohol is mixed, difficulty in separating the mixed alcohol, etc.

However, the integrated reaction system for the ester composition according to the present invention may greatly reduce redundant process facilities due to the application of high efficiency gas-liquid separation column and mixed alcohol separation column, reduce a factory site by one half or more, and thus, obtain economical efficiency due to reduction in production costs, process operating expenses, etc., and maximize the efficiency due to the simplified process, compared to the conventional system in which the process for preparing the ester compound and the process for preparing the ester composition using the ester compound have been used in combination.

Figure 2:
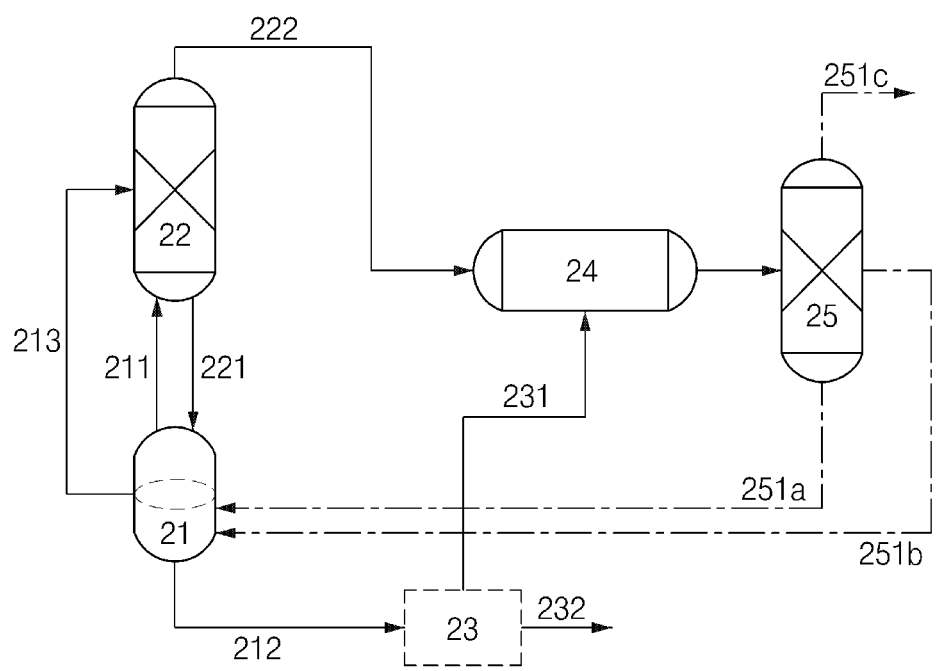
FIG. 2 is a process flow chart illustrating an example of a process for preparing an ester composition according to a preparation system of the present invention.

FIG. 2 illustrates an example of a process flow chart of the preparation system according to the present invention.

Referring to FIG. 2, in the integrated reactor 21, the direct esterification and the trans-esterification may be carried out sequentially in the same space, so that facilities may be reduced compared to the case where two reactors have been used. Through the introduction of the mixed alcohol separation column 25, it is possible to separate the first alcohol and the second alcohol and recirculate them suitably for each reaction cycle to the reactor even if the two kinds of alcohol and other by-products having low boiling points flow together into the alcohol storage tank 24.

In addition, in the conventional process, separate reactors and separate separation processes (facilities, such as a condenser, a reflux bath, etc., including a separation column) exist, so that a continuous process and a batch process coexist, and therefore, facilities for linking the continuous process and the batch process are necessarily included in a design. However, as in the present invention, if the reactors are integrated and the separation processes are integrated so as to enables the separation of the mixed alcohol, process operation may be carried out even if the facilities such as the buffer tanks 16a and 16b are removed.

Specifically, the beginning carboxylic acid-based compound including two or more carboxyl groups and the first alcohol may be put into the integrated reactor 21 to start the reaction, and the ester compound, the unreacted first alcohol, the carboxylic acid-based compound including two or more carboxyl groups, and as a by-product, moisture may be produced by the direct esterification.

The water generated as the by-product of the esterification must be necessarily removed during the direct esterification. The water removal may be carried out through the gas-liquid separation column 22. Specifically, during the direct esterification, the gas phase low boiling point compound may flow out through the upper outlet line 211 of the integrated reactor 21. Herein, the low boiling point compound may include water and the first alcohol. Herein, the water and the first alcohol are separated through the gas-liquid separation column 22 and a condenser (not shown) connected to the top of the column and a decanter (not shown). The first alcohol may be refluxed and then flow again into the reactor and the water may be removed. The first alcohol recovered through the reflux may be recovered through an inlet line. The inlet line may be connected to the bottom of the gas-liquid separation column 22 so that the first alcohol may be recovered to the integrated reactor 21 through the lower recovery line 221.

When the direct esterification ends, for the trans-esterification, the second alcohol may be put into the integrated reactor 21. In order to proceed the reaction toward the product in the trans-esterification reaction, which is an equilibrium reaction, it is necessary to remove the first alcohol, which is the product, before the input of the second alcohol. The removal of the first alcohol may be carried out through the gas-liquid separation column 22.

The direct esterification product gasified in the integrated reactor 21 and the gas phase low boiling point mixture may flow out through the upper outlet line 211 of the integrated reactor 21 and flow into the gas-liquid separation column 22. Herein, the transfer to the gas-liquid separation column 22 may be carried out by reduction in pressure. The gas-liquid separation of the gas phase materials which have flowed into the gas-liquid separation column 22 may be carried out by boiling point difference and mass transfer in the gas-liquid separation space in the column. The gasified direct esterification product liquefies again and flows back to the reactor through the lower recovery line 221 of the gas-liquid separation column 22. The first alcohol, as the low boiling point mixture, may flow through the upper outflow line 222 into the alcohol storage tank 24 and be stored therein.

Due to the small mass transfer area and low efficiency of the transfer of the gas phase materials in the integrated reactor 21 to the gas-liquid separation column by reduction in pressure, it is possible to make the ungasified low boiling point mixture and the liquid phase direct esterification product flow, preferably through the middle outlet line 213 provided in order to be connected to the liquid phase compartment of the integrated reactor 21. The middle outlet line 213 may be connected to the side part at one half or higher in the height direction of the gas-liquid separation column 22. A power device for sending the liquid phase material in the liquid phase compartment in the reactor to the gas-liquid separation column 22 (not shown) may be provided with the middle outlet line and the power device may be a variety of pumps (not shown). The provision of the integrated reactor 21 with the middle outlet line for flow into the gas-liquid separation column 22 may maximize the gas-liquid separation efficiency due to the increase in the mass transfer area, so as to remove the unreacted first alcohol to a desired level in the reactor within a short time.

The first alcohol removed from the gas-liquid separation column 22 may flow into the alcohol storage tank 24, be stored thereat, and after a certain period of time or immediately thereafter, flow into the mixed alcohol separation column 25, where the process of separating the first alcohol and the second alcohol may be carried out.

Meanwhile, after the end of the direct esterification and the removal of the unreacted first alcohol in the integrated reactor 21, for the trans-esterification, the second alcohol may be put into the integrated reactor 21.

Herein, a reactant supply part (not shown) may be present in the integrated reactor 21. All of the reactants, such as the carboxylic acid-based compound including two or more carboxyl groups, the first alcohol, the second alcohol, and the like, may be injected through one reactant supply part. Each supply part may also be provided and each of the reactants may be injected through the each supply part. In addition, after one cycle of the reaction, from the alcohol storage tank 24, the mixed alcohol is separated through the mixed alcohol separation column 25, so that the first alcohol and the second alcohol may be injected into the reactor through the alcohol recirculation lines 251a and 251b.

After the input of the second alcohol, the trans-esterification with the ester compound, which is the product of the direct esterification, may be carried out in the integrated reactor 21, and the subsequent process may be similar to the direct esterification. Also in the middle of the trans-esterification, as in the direct esterification, the first alcohol gasified through the gas-liquid separation column 22 and the second alcohol may be recovered through a condenser (not shown) and a decanter (not shown) again to the integrated reactor 21.

When the trans-esterification is completed, the product of the trans-esterification may be subjected to a purification process for commercialization and the product may be passed through the lower outlet line 212 of the integrated reactor and flow into the purification unit 23. In the purification unit 23, the product purification may be carried out by using a facility including one or more purification baths, condensers, etc.

In the purification unit 23, by-products or unreacted materials may be removed from the product. Accordingly, the separated unreacted second alcohol, the first alcohol which is the by-product, and the like, may flow through the alcohol recovery line 231 to the alcohol storage tank 24. After the inflow to the alcohol storage tank 24, the process of appropriate separation in the alcohol separation column 25 and recirculation to the integrated reactor 21 may be carried out.

The stream having the unreacted material, etc. removed from the product may flow to the product storage tank (not shown) through the purified product line 232, and the product stored in the storage tank may be commercialized through a predetermined process.

The first alcohol and the second alcohol removed from the purification unit 23 may flow into the alcohol storage tank 24, be stored thereat, and after a certain period of time or immediately thereafter, flow into the mixed alcohol separation column 25, where the process of separating the first alcohol and the second alcohol may be carried out and the first alcohol and the second alcohol may be recirculated to the integrated reactor 21 suitably for the reaction time through the alcohol recirculation lines 251a and 251b. In this column, water present as the by-product may also be separated, so as to be removed through the upper discharge line 251c.

Although not shown in FIGS. 1 and 2, devices generally included in a process design, such as a heat exchanger, a condenser, a reboiler, a pump, etc. may also be included in a design by a person skilled in the art and be disposed appropriately according to the design.

Ester Composition Preparation Method

According to another embodiment of the present invention, an ester composition preparation method, including: the step S1 of preparing an ester compound and moisture through the direct esterification of a carboxylic acid-based compound including two or more carboxyl groups and a first alcohol in an integrated reactor; the step S2 of removing a low boiling point mixture including the unreacted first alcohol and the moisture in the integrated reactor and recovering the first alcohol to an alcohol storage tank; the step S3 of putting a second alcohol into the integrated reactor and preparing an ester composition through the trans-esterification of the ester compound and the second alcohol; and the step S4 of purifying the ester composition and recovering a mixed alcohol to an alcohol storage tank, is provided.

The preparation method is a method applied in the above described preparation system, and all of a series of processes are the same as those described above, and the description of the raw materials for reaction is also the same as that described above. Therefore, the description thereof will be omitted.

However, in the step S2, when the unreacted first alcohol is removed, in the integrated reactor, it is preferable to remove the unreacted first alcohol so as to be 2 weight % or less based on the total weight of materials in the reactor. It may be preferable to use the above described middle outlet line together to remove the unreacted first alcohol to such level within a short time.

Specific reaction conditions (temperature, pressure, time, etc.) of the direct esterification and the trans-esterification may be (but not particularly limited to) reaction conditions applied in the art.

EXAMPLES

Hereinafter, the present invention will be described in more detail by examples. However, the following examples are for illustrative purposes only and the scope of the present invention is not limited thereto.

In the following examples 1 and 2 and comparative example 1, the system including the removal unit according to the present invention was simulated by using BATCH MODELER within the commercial process simulation program, ASPEN PLUS.

Example 1

As raw materials for reaction, terephthalic acid and 2-ethyl hexanol were introduced into the integrated reactor 21, so as to conduct the direct esterification. Then, butanol was introduced into the integrated reactor 21, so as to conduct the trans-esterification, and then the reaction was completed. According to the process flow chart shown in FIG. 2, the ester composition preparation process was carried out. In the middle of the direct esterification and the trans-esterification, the removal of 2-ethyl hexanol was carried out through the middle outlet line and the upper outlet line. The results are shown in Table 1 below.

Example 2

The ester composition preparation process was carried out in the same manner as in Example 1 except that 2-ethyl hexanol was removed only through the upper outlet line without the application of the middle outlet line of the integrated reactor in the middle of the direct esterification and the trans-esterification. The results are shown in Table 1 below.

Comparative Example 1

As raw materials for reaction, terephthalic acid and 2-ethyl hexanol were introduced into the first reactor 11a, so as to conduct the direct esterification. Then, simulation was conducted according to the process flow chart shown in FIG. 1. Butanol was introduced into the second reactor 11b, so as to conduct the trans-esterification, and then the reaction was completed. The results of the process simulation conducted according to the process flow chart shown in FIG. 1 are shown in Table 1 below.

TABLE 1

|  |  | Example 1 | Example 2 | Comparative example 1 |
|---|---|---|---|---|
| Introduced amount of raw material (kg) | Terephthalic acid | 5.0 | 5.0 | 5.0 |
|  | 2-Ethyl hexanol | 6.5 | 6.5 | 8.3 |
|  | Butanol | 1.2 | 1.2 | 2.3 |
| Product yield (kg) |  | 10.9 | 10.9 | 10.9 |
| One cycle process execution time (hr) |  | 18.7 | 19.2 | 19.8 |
| Time required for the transfer process (min) |  | 40 | 40 | 110 |

As can be seen from Table 1 above, it can be found that the process time in Examples 1 and 2, to which the integrated process was applied, was greatly shortened compared to the process time in Comparative example, in which separate processes were carried out. Considering that the time is required for one cycle, it may lead to considerable time reduction from the viewpoint of the overall product supply and demand, and consequently, result in improvement in productivity. That is, it was found that application of the preparation system, for which the integrated reactor was used, of the present invention, may increase the productivity.

When the introduced amounts of raw materials were compared, it can be found that the amounts of 2-ethyl hexanol and butanol added in Examples 1 and 2 were greatly reduced compared to those in Comparative Example. It can be found that in the case of Examples 1 and 2, the mixed alcohol separation column, by which the mixed alcohol is not discarded and can be reused, was introduced, and thus, the content of the raw material alcohol to be newly added may be reduced.

In addition, the time spent transferring which should be improved in terms of the process operating efficiency was evaluated, and as a result, it can be found that the transfer time in Examples 1 and 2 was shortened by about ⅓, compared to that in Comparative example. From this, it can be found that application of the ester composition preparation system according to the present invention may enable the efficient operation of process.

Furthermore, it can be also found that the process time in Example 1, in which the middle outlet line was applied for the removal of the first alcohol, that is, 2-ethyl hexanol, through the gas-liquid separation column in the integrated reactor, was more shortened, due to the increase in the gas-liquid separation efficiency, than the process time in Example 2.

DESCRIPTION OF REFERENCE NUMERALS

| Description of Reference Numerals | | | |
|---|---|---|---|
| 11a: | First reactor | 11b: | Second reactor |
| 12a: | First gas-liquid separation column | | |
| 12b: | Second gas-liquid separation column | | |
| 13: | Purification bath | 14a: | Alcohol tank |
| 14b: | Mixed alcohol tank | 16a: | First buffer tank |
| 16b: | Second buffer tank | | |
| 17: | Unreacted alcohol removal column | | |
| 18: | Neutralizer | | |
| 21: | Integrated reactor | | |
| 22: | Gas-liquid separation column | | |
| 23: | Purification unit | 24: | Alcohol storage tank |
| 25: | Mixed alcohol separation column | | |
| 211: | Upper outlet line | 212: | Lower outlet line |
| 213: | Middle outlet line | 221: | Lower recovery line |
| 222: | Upper outflow line | 231: | Alcohol recovery line |
| 232: | Purified product line | | |
| 251a: | First alcohol circulation line | | |
| 251b: | Second alcohol circulation line | | |

The invention claimed is:

1. A preparation system, comprising:
an integrated reactor having an inner reaction space in which a direct esterification, which is a reaction of a first alcohol and a carboxylic acid-based compound comprising two or more carboxyl groups, and a trans-esterification, which is a reaction of a product of the direct esterification and a second alcohol, are carried out, an upper outlet line connected to a gas phase compartment, and a lower outlet line connected to a liquid phase compartment, provided therewith;
a gas-liquid separation column having a gas-liquid separation space, into which a gasified reaction product and a gas phase low boiling point mixture from the integrated reactor flow through the upper outlet line of the integrated reactor and in which a gas-liquid separation is carried out, a lower recovery line, through which a liquefied reaction product is recovered to the integrated reactor, and an upper outflow line, through which the gas phase low boiling point mixture flows out, provided therewith;
a purification unit having a purification bath, in which an ester composition flowed out through the lower outlet line of the integrated reactor and the second alcohol are separated, a purified product line through which a purified ester composition is discharged, and an alcohol recovery line through which the second alcohol is recovered, provided therewith;
an alcohol storage tank having an inner space, in which the first alcohol and the second alcohol are stored, provided therewith, and connected to the upper outflow line of the gas-liquid separation column and to the alcohol recovery line of the purification unit, so as to store a mixed alcohol of the first alcohol and the second alcohol; and
a mixed alcohol separation column having an alcohol separation space, into which the mixed alcohol flows from the alcohol storage tank and in which the mixed alcohol is separated depending on the number of alkyl carbon atoms of the alcohol, and one or more recirculation lines, through which separated alcohol is recirculated, provided therewith,
wherein the reaction product in the gas-liquid separation column is a product of the direct esterification or a product of the trans-esterification, and the low boiling point mixture includes one or more of the first alcohol and the second alcohol.

2. The preparation system of claim 1, wherein the preparation system further has a middle outlet line provided with the liquid phase compartment in the integrated reactor, and the middle outlet line is connected to the middle part of the gas-liquid separation column and the middle part of the gas-liquid separation column is positioned at one half or higher in the height direction of the column.

3. The preparation system of claim 2, wherein through the middle outlet line of the integrated reactor, a liquid phase reaction product of the direct esterification and a low boiling point mixture including an ungasified first alcohol flow out.

4. The preparation system of claim 1, wherein the one or more recirculation lines of the mixed alcohol separation column comprises a recirculation line for the first alcohol and a recirculation line for the second alcohol.

5. The preparation system of claim 1, further comprising a product storage tank, wherein the product storage tank is connected to the purified product line of the purification unit.

6. The preparation system of claim 1, which is a batch reaction system.

7. The preparation system of claim 1, wherein the carboxylic acid-based compound comprising two or more carboxyl groups is terephthalic acid.

8. The preparation system of claim 1, wherein the first alcohol and the second alcohol are primary alcohols, and the number of carbon atoms of the first alcohol is larger than that of the second alcohol.

9. The preparation system of claim 1, wherein the numbers of alkyl carbon atoms of the first alcohol and the second alcohol are 1 to 12.

10. The preparation system of claim 1, wherein the ester composition is a mixture of three ester compounds.

\* \* \* \* \*